(12) United States Patent
Czapiewski et al.

(10) Patent No.: US 7,980,146 B2
(45) Date of Patent: Jul. 19, 2011

(54) SYSTEM FOR SAMPLING THE AIRFLOW ENTERING THE COMPRESSOR OF A TURBOMACHINE

(75) Inventors: Jeff P. Czapiewski, Greer, SC (US); Rahul J. Chillar, Marietta, GA (US); Steve D. Hiner, Salisbury (GB); Rebecca E. Hefner, Greenville, SC (US); William K. Eyers, Chobham (GB); Stephen F. Banks, Yateley (GB)

(73) Assignee: General Electric Company, Schenectady, NY (US)

( * ) Notice: Subject to any disclaimer, the term of this patent is extended or adjusted under 35 U.S.C. 154(b) by 627 days.

(21) Appl. No.: 12/175,907

(22) Filed: Jul. 18, 2008

(65) Prior Publication Data

US 2010/0011886 A1    Jan. 21, 2010

(51) Int. Cl.
*G01N 1/22* (2006.01)
(52) U.S. Cl. .................................................. 73/863.23
(58) Field of Classification Search ............... 73/863.61, 73/863.23
See application file for complete search history.

(56) References Cited

U.S. PATENT DOCUMENTS

| 4,978,506 A | 12/1990 | Calderwood | 422/73 |
| 5,353,650 A | 10/1994 | Barshay et al. | 73/863.02 |
| 2002/0153873 A1* | 10/2002 | Shapiro et al. | 324/71.2 |

* cited by examiner

*Primary Examiner* — Hezron E Williams
*Assistant Examiner* — Tamiko Bellamy
(74) *Attorney, Agent, or Firm* — Dale J. Davis; Ernest G. Cusick; Frank A. Landgraff

(57) ABSTRACT

An embodiment of the present invention provides an air sampling system for measuring corrosives within an airstream flowing within an inlet system. This air sampling system may include an air sampling unit with a plurality of sampling coupons secured within. Parts of the air sampling system may be externally mounted to the inlet system, allowing for an operator to access the sampling coupons, while the inlet system operates. In operation, an embodiment of the present invention has a sampling line connected to the air sampling system; the airstream flowing within the sampling line passes over the sampling coupons and then returns to the inlet system.

28 Claims, 4 Drawing Sheets

SYSTEM FOR SAMPLING THE AIRFLOW ENTERING THE COMPRESSOR OF A TURBOMACHINE

BACKGROUND OF THE INVENTION

The present invention relates generally to the air entering a turbomachine; and more particularly to a system for sampling the airstream entering the inlet system.

Some turbomachines, such as, but not limiting of, gas turbines, and aero-derivatives, have an air inlet system that channels the incoming airstream towards a compressor. The inlet system usually has a filter section, which screens the airstream of foreign objects and other undesired materials. Typically, the inlet system and the compressor are created out of metals that may corrode due to the environment (ambient conditions, etc) in which the turbomachine operates. Industry standards provide techniques for monitoring the corrosive rate of an environment.

These turbomachines may develop microenvironments related to the ambient conditions in which the turbomachine operates. These microenvironments, which have accelerated airflows and pressures, typically increase the corrosion rate of the components of the compressor. Therefore, to accurately determine the corrosion rate, one should not simply measure the ambient conditions and make a conclusion on the airstream and the microenvironment. The airstream downstream of the filter section should be monitored to determine the environmental effects of the airstream on the compressor components.

One method of determining the corrosion rate in the microenvironment is to place strips (hereinafter "coupons") in the airstream. Overtime, the coupons become corroded and fail. A user monitors the coupons and a time to failure. The coupons may be sent to a lab to determine the type(s) or corrosives that caused the failure.

There are a few concerns with the described method of determining the corrosion rate. A coupon within the inlet system may corrode, dislodge, and become a projectile within the inlet, potentially causing damage to the compressor components. Additionally, placing the coupons in the inlet channel may create flow distortion waves, which can also damage turbomachine components.

For the foregoing reasons, there is a need for a system that measures the corrosives within an airstream flowing in an inlet system. The system should monitor the corrosion rate of the inlet system. The system should not create distortion waves when used.

BRIEF DESCRIPTION OF THE INVENTION

In an embodiment of the present invention, a sampling system for an inlet system, the sampling system comprising: at least one sampling unit for measuring corrosives within the airstream flowing within the inlet system, the at least one sampling unit comprising: a lid for accessing an internal portion of the at least one sampling unit; a sampling chamber within the internal portion, wherein the sampling chamber comprises: a mounting system for securing at least one sampling coupon, wherein the mounting system defines at least one position; wherein the mounting system allows for the at least one sampling coupon to be secured at the at least one position; flow straightener for directing the airstream to flow over the at least one sampling coupon, wherein the flow straightener comprises an upstream portion located adjacent a supply line and a downstream portion located adjacent a discharge line; wherein the upstream and downstream portions extend approximately the width of the sampling chamber; a flow balancer for filtering foreign objects from the airstream, wherein the depth of the flow balancer nearly equals the depth of the sampling chamber; and wherein the flow balancer is located between the downstream portion of the flow straightener and the discharge line; and an air amplifier for assisting with moving the airstream through the sampling chamber; wherein portions of the airstream enter a supply line, flow through the sampling chamber, exit via a discharge line and reenter the inlet system.

In an alternate embodiment of the present invention, a system recording corrosives within an airstream entering a turbomachine, the system comprising: an inlet system for receiving and directing air into a compressor of the turbomachine, wherein the inlet system comprises at least one of the following: an inlet filter house for screening the airstream entering the inlet system; a cooling module for conditioning the airstream within the inlet system; a silencer section for reducing the noise within the inlet system; and an inlet bleed heat system for conditioning the airstream; a sampling system mounted outside of an inlet system, the sampling system comprising: at least one sampling unit for recording the level of corrosives in the airstream, the at least one sampling unit comprising: a lid for covering internal components of the at least one sampling unit; wherein the lid is created from a material that allows for viewing the internal components after the lid is closed; a sampling chamber within the sampling unit, wherein the sampling chamber comprises: a shelf for supporting sampling coupons within the sampling chamber, wherein the shelf includes individual positions and allows for each sampling coupon to be secured at an individual position; flow straightener for directing the airstream to flow in a nearly uniform manner over each sampling coupon, wherein the flow straightener comprises an upstream portion located positioned adjacent a supply line and a downstream portion positioned located adjacent a discharge line; wherein the upstream and downstream portions are in parallel position and extended approximately the width of the sampling chamber; a flow balancer for preventing the chance of a foreign objects from entering the inlet system, wherein the depth of the flow balancer nearly extends to the depth of the sampling chamber; and wherein the flow balancer is located between the downstream portion of the flow straightener and the discharge line; and an air amplifier for moving the airstream throughout the sampling chamber and for returning the airstream back into inlet system; wherein portions of the airstream enter a supply line, flow through the sampling chamber, exit via a discharge line and reenter the inlet system.

BRIEF DESCRIPTION OF THE DRAWINGS

These and other features, aspects, and advantages of the present invention will become better understood when the following detailed description is read with reference to the accompanying drawings in which like characters represent like elements throughout the drawings.

DETAILED DESCRIPTION OF THE INVENTION

The following detailed description of preferred embodiments refers to the accompanying drawings, which illustrate specific embodiments of the invention. Other embodiments having different structures and operations do not depart from the scope of the present invention.

Certain terminology is used herein for the convenience of the reader only and is not to be taken as a limitation on the scope of the invention. For example, words such as "upper", "lower", "left", "right", "front", "rear", "top", "bottom", "horizontal", "vertical", "upstream", "downstream", "fore", "aft", and the like; merely describe the configuration shown in the Figures. Indeed, the element or elements of an embodiment of the present invention may be oriented in any direction and the terminology, therefore, should be understood as encompassing such variations unless specified otherwise.

An embodiment of the present invention provides an air sampling system for measuring corrosives within an airstream flowing within an inlet system of a turbomachine. This air sampling system may include an air sampling unit with a plurality of sampling coupons secured within. Parts of the air sampling unit may be externally mounted to the inlet system, allowing for an operator to access the sampling coupons, while the turbomachine is in operation.

In operation, an embodiment of the present invention has a sampling line connected to the air sampling unit, the airstream flowing within the sampling line passes over the sampling coupons and then returns to the inlet system. The coupons are monitored; and then removed to determine the level of corrosives within the airstream. The corrosion rate of the coupons may correlate to pitting that occurs on the compressor components, such as blades and other components. This correlation may be useful in developing turbomachine maintenance schedules, etc.

Figure 1:
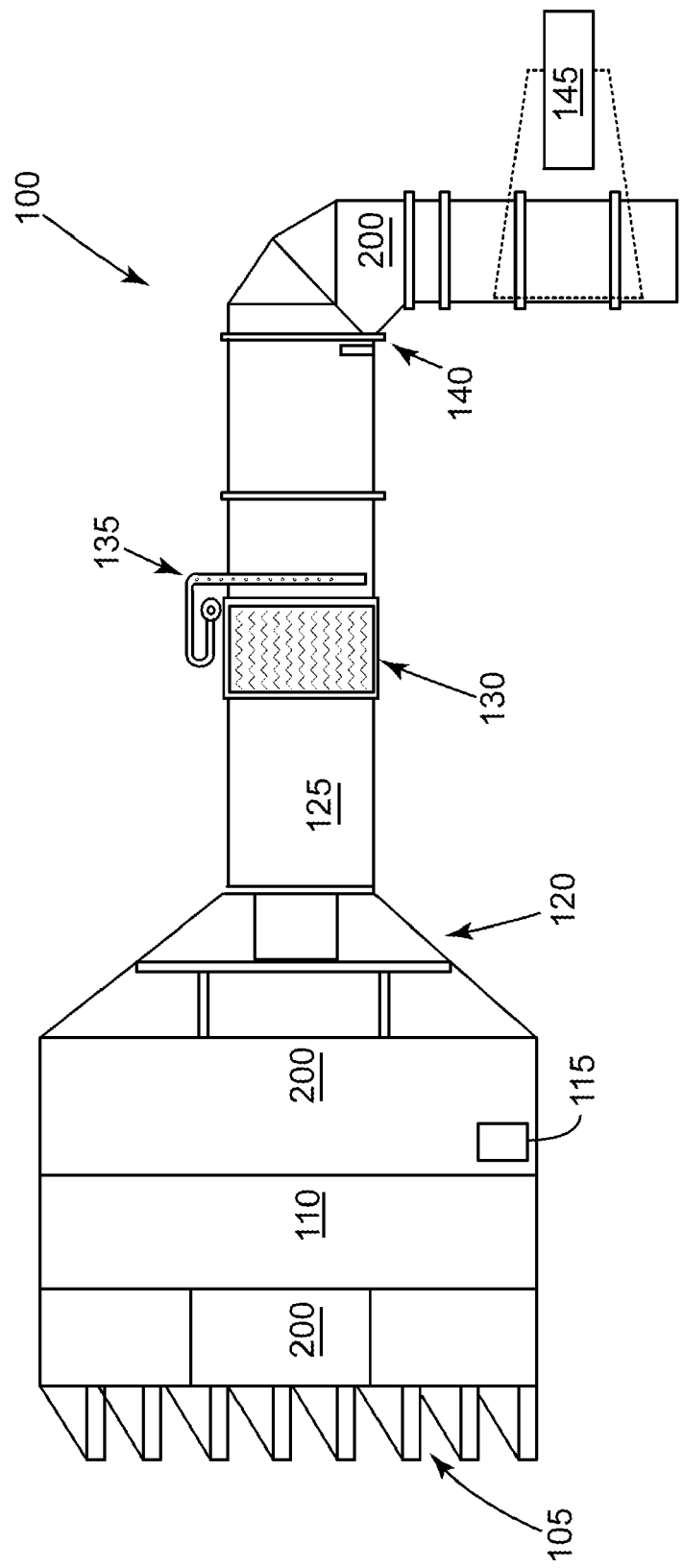
FIG. 1 is a schematic illustrating an environment where an embodiment of the present invention may operate.

Referring now to the Figures, where the various numbers represent like elements throughout the several views, FIG. 1 is a schematic illustrating an environment where an embodiment of the present invention may operate. FIG. 1 illustrates an inlet system 100 that is typically integrated with a compressor 145 of a turbomachine (not illustrated). The following description provides an overview of a typically configuration of an inlet system 100; the present invention may be used with other configurations of the inlet system 100, which are not illustrated in the Figures.

The inlet system 100 channels the airstream drawn in by the compressor 145. The airstream usually comes from the environment in which the turbomachine operates. Initially, the airstream flows around a weather hood 105, which may prevent weather elements, such as rain, snow, etc, from entering the compressor 145. The airstream may then flow through an inlet filter house 110; which generally removes foreign objects and debris from the airstream. Next, the airstream may flow through a cooling module 115, such as, but not limiting of, a water washing system. Next, the airstream may flow through a transition piece 120 and an inlet duct 125; these components may adjust the velocity and pressure of the airstream. Next, the airstream may flow through a silencer section 130. Next, the airstream may flow through an inlet bleed heat system 135, which generally increases the airstream temperature prior to entering the compressor 145. A trash screen 140, or the like, may be located downstream of the inlet duct 125 and generally serves to prevent debris from entering the compressor 145.

An embodiment of the present invention may provide multiple air sampling systems 200, with each system 200 positioned in varying locations on the inlet system 100. As illustrated in FIG. 1, a first air sampling system 200 may positioned upstream of the inlet filter house 110; a second air sampling system 200 may positioned downstream of the inlet filter house 110; and a third air sampling system 200 may be positioned downstream of the inlet silencer section 130.

Figure 2:
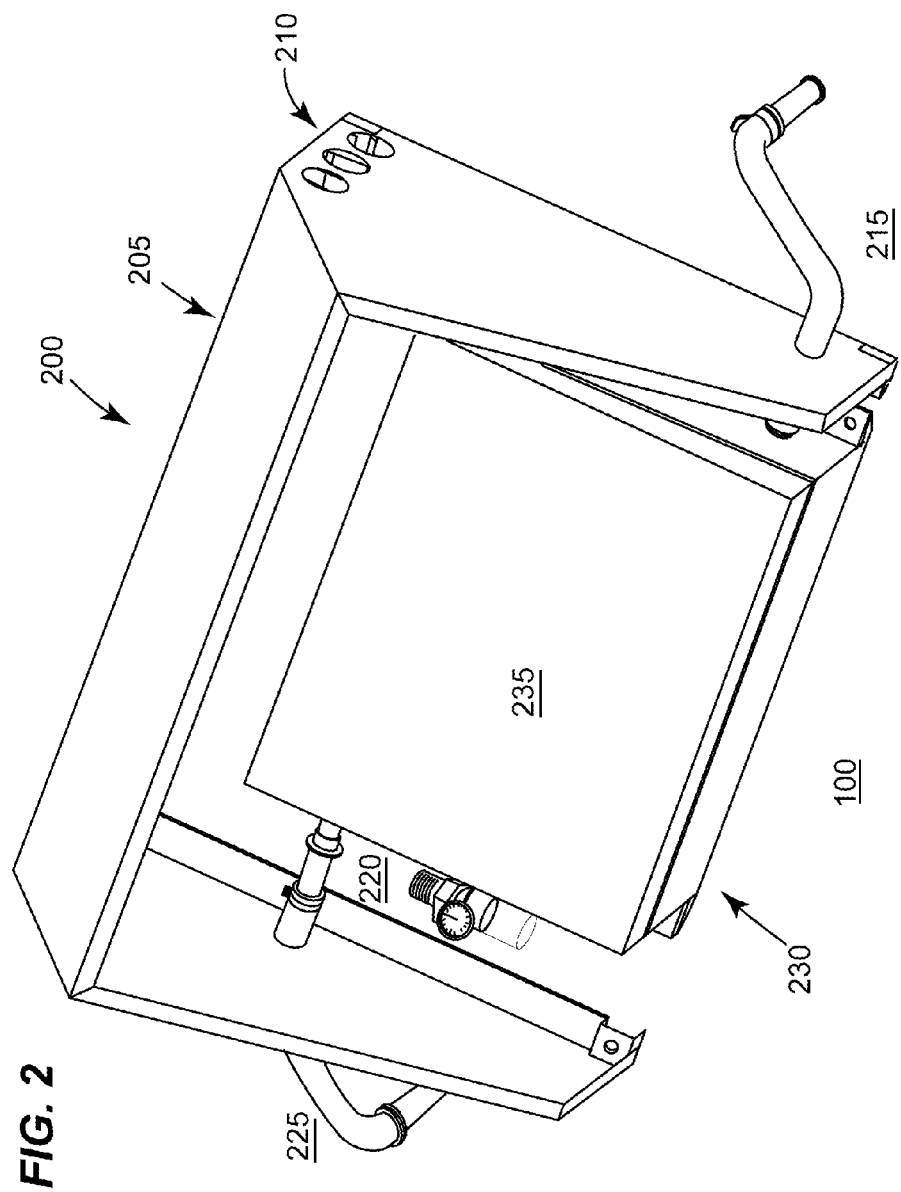
FIG. 2 is a schematic illustrating an isometric view of an air sampling system, in accordance with an embodiment of the present invention.

FIG. 2 is a schematic illustrating an isometric view of an air sampling system 200, in accordance with an embodiment of the present invention. The components of an embodiment of the air sampling system 200 may comprise: a weather hood 205, which may have a plurality of ventilation holes 210; an airstream supply line 215; an air amplifier 220; an airstream discharge line 225; a sampling unit 230 having a lid 235.

Figure 3:
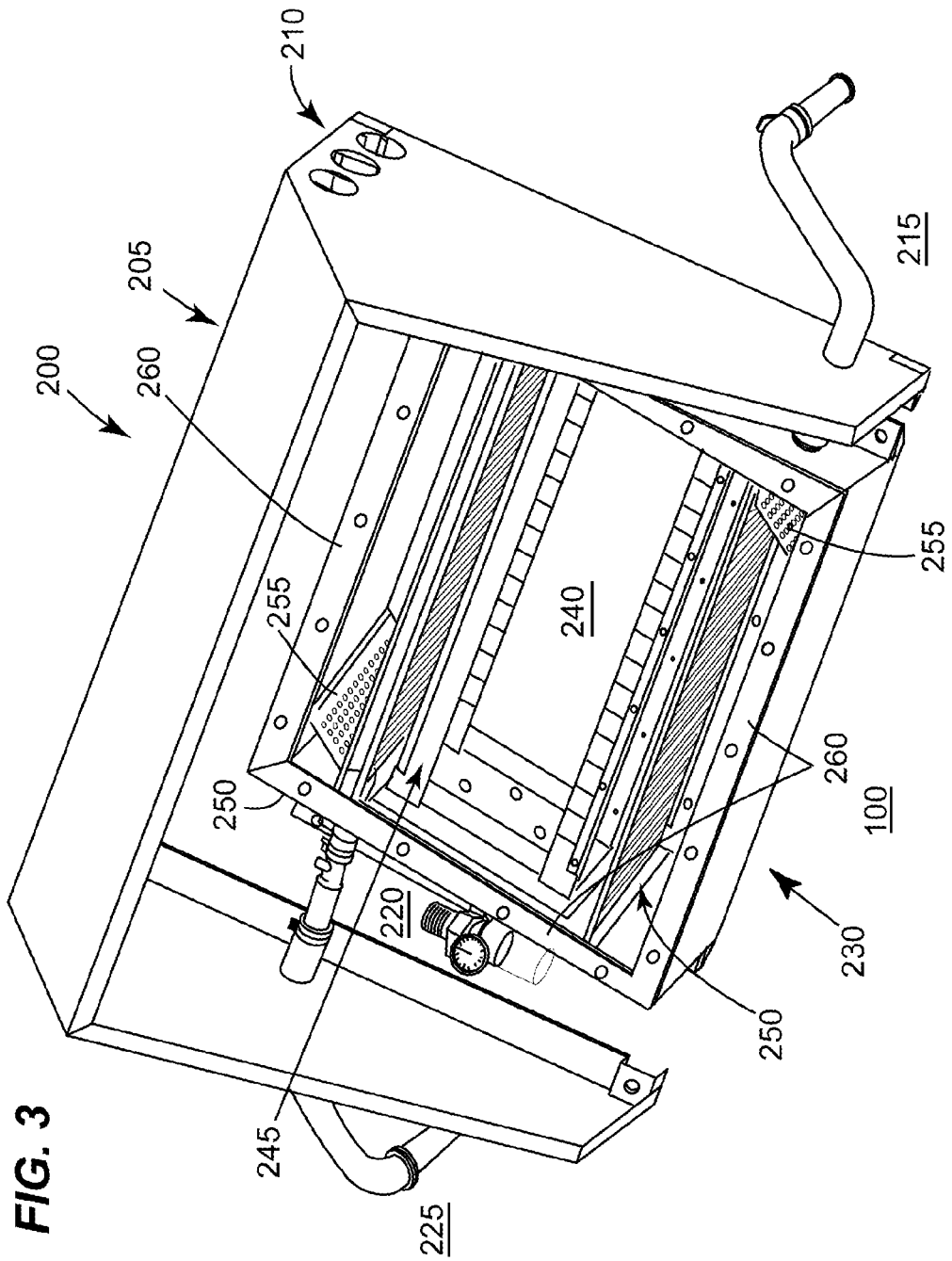
FIG. 3 is a schematic illustrating an isometric view of an air sampling system without sampling coupons installed, in accordance with an embodiment of the present invention.
Figure 4:
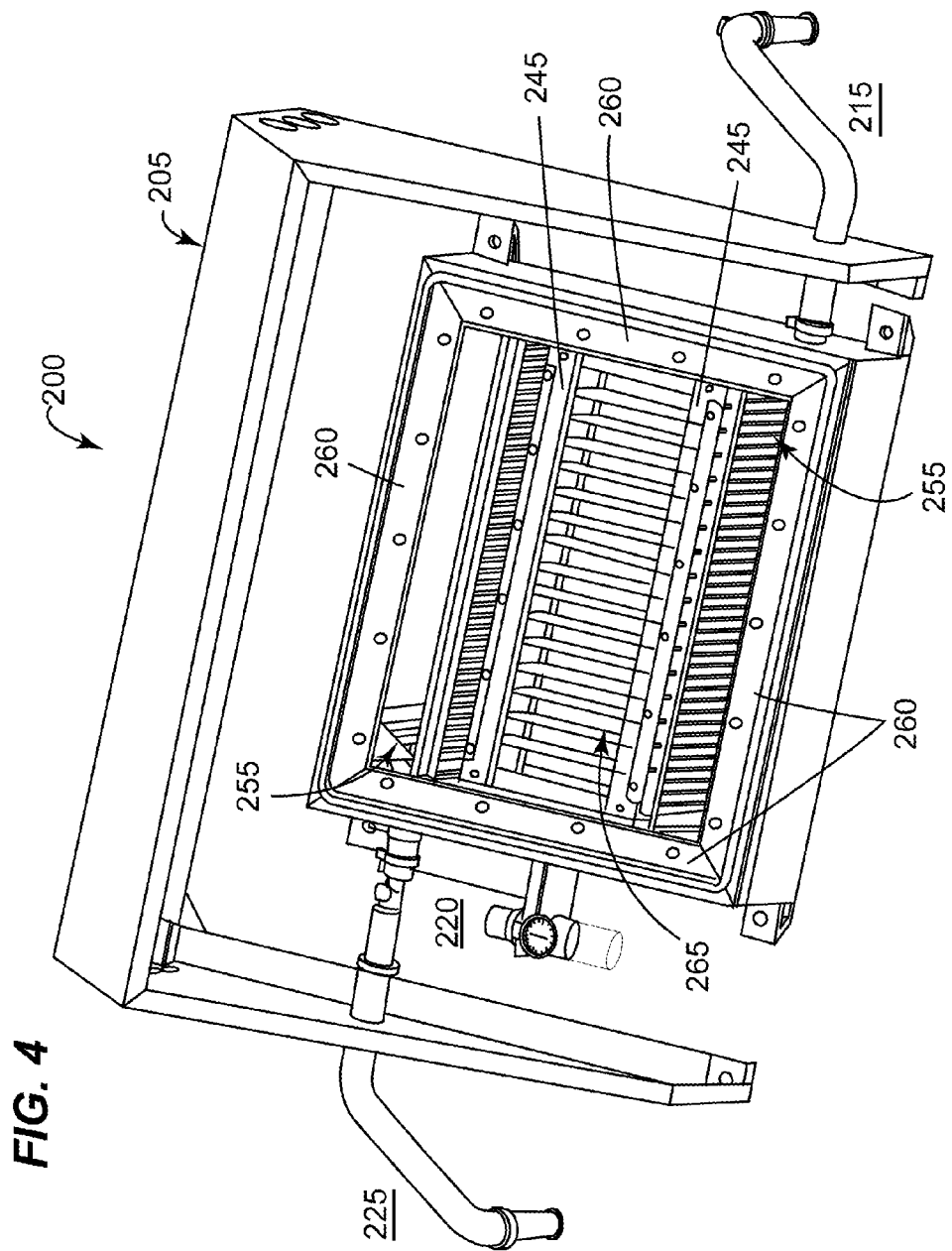
FIG. 4 is a schematic illustrating an isometric view of an air sampling system with sampling coupons installed, in accordance with an embodiment of the present invention.

As illustrated in FIGS. 2-4, the weather hood 205 may shield portions of sampling unit 230 from the elements, such as, but not limiting of, the sun, rain, sleet, snow, hail, or the like. The ventilation holes 210 may exist on one or both sides of the weather hood 205 and may increase air circulation around the sampling unit 230. The weather hood 205 may be created out any material capable of withstanding the environment in which the sampling unit 230 is exposed. For example, but not limiting of, the weather hood 205 may be created out of a stainless steel, a plastic, or the like.

The supply line 215 serves to link an internal portion of the inlet system 100, with the sampling unit 230. The supply line 215 may include a first end connected to the inlet system 100 and a second end connected to an inlet portion of the sampling unit 230. The supply line 215 may be created out of any material capable of withstanding the operating environment of the inlet system 100 and the air sampling system 200. The supply line 215 maybe sized to provide a desired pressure, flowrate, and velocity of the airstream entering the sampling unit 230.

The discharge line 225 serves to a discharge portion of the sampling unit 230 with the inlet system 100. The discharge line 225 may include a first end connected to the inlet system 100 and a second end connected to an outlet portion of the sampling unit 230. The discharge line 225 may be created out of any material capable of withstanding the operating environment of the inlet system 100 and the air sampling system 200. The discharge line 225 maybe sized to provide a desired pressure, flowrate, and velocity of the airstream exiting the sampling unit 230. An embodiment of the present invention may include a discharge line 225 comprising an air amplifier 220. The air amplifier 220 serves to move the airstream through the sampling unit 230. The air amplifier 220 may take the form of: for example, but not limiting of, a suction fan that draws the airstream over the sampling coupons 265; illustrated in FIGS. 3 and 4 and described below. The physical characteristics of the air amplifier 220 are generally determined by the type of inlet system 100 and turbomachine in which the air sampling system 200 operates. In an embodiment of the present invention the air amplifier 220 may only require a compressed air source, common on a turbomachine site.

The sampling unit 230 allows the air sampling system 200 to extract the airstream from the inlet system 100, distributes the airstream over a plurality of sampling coupons 265, and then re-injects the airstream into the inlet system 100. The lid 235 allows for the sampling unit 230 to form a sealed environment for measuring the corrosives within the airstream. In an embodiment of the present invention, the lid 235 may be created out of a transparent material. Here, a user may view the sampling coupons 265 without opening the lid 235. The lid 235 may also allow a user to remove and/or exchange sampling coupons 265 while the turbomachine operates.

In an alternate embodiment of the present invention, the lid 235 comprises an external section and an internal section. Here, the external section may serves to enclose the sampling unit 230 and is the overall cover. The external section may be created out of a material that protects the internal section and shields the internal components of the sampling unit 230. This material may be, for example, but not limiting of, the same material as the external portions of the sampling unit 230. The external section may protect from the environmental effects that the sampling unit 230 may be exposed. These effects may be for example, but not limiting of, ultraviolent rays, radiation heating, debris, precipitation, or combinations thereof.

The internal section of this embodiment of the lid 235 may serve as a see-through barrier between the external section and the internal components of the sampling unit 230. The internal section may aide in maintaining a sealing environment within the sampling unit 230. The internal section may be created out of a transparent material that allows for observing the internal components of the sampling chamber without exposures to the environment.

This alternate embodiment allows the user to observe the internal components of the sampling unit 230 without comprising the integrity of the air sampling system 200. Here, the sealing of the air sampling system 200 may be maintained.

Referring now to FIGS. 3 and 4. FIG. 3 is a schematic illustrating an isometric view of the sampling unit 230 of FIG. 2 with the lid 235 removed and without sampling coupons 265 installed, in accordance with an embodiment of the present invention. FIG. 4 is a schematic illustrating an isometric view of the sampling unit 230 of FIG. 2 with the lid 235 removed and with sampling coupons 265 installed, in accordance with an embodiment of the present invention.

The sampling unit 230 may enclose: a sampling chamber 240; a mounting system 245; flow straighteners 250; flow balancers 255: insulation 260; and sampling coupons 265 (illustrated in FIG. 4). The sampling chamber 240 may be considered the area within the sampling unit 230 that the airstream engages the sampling coupons 265. The sampling chamber 240 may have at least one mounting system 245, which secures at least one sampling coupon 265. The sampling chamber 240 encloses an area larger enough to allow the airstream to uniformly flow across each sampling coupon 265. The sampling chamber 240 generally allows for the airstream to flow into throughout. The flow straightener 250 may define a forward and an aft boundary wall of the sampling chamber 240. The flow straightener 250 adds a pressure drop within the sampling unit 230 and to help balance the flow of the airstream, allowing for uniform flow across the sampling coupons 265. The flow straightener 250 may have the form of: for example, but not limiting of, a mesh screen, a honeycomb flow separators, a perforation sheet; or the like. The width of the flow straightener 250 may be similar to the width of the sampling chamber 240.

In an alternate embodiment of the present invention the flow straightener 250 comprises: a fore portion, an aft portion, a filter section between the fore and aft portions. Here, the filter section serves to capture some of the debris within the airstream and/or on the sampling coupons 265.

An upstream flow balancer 255 may be located adjacent the supply line 215 and a downstream flow balancer 255 adjacent the discharge line 225 (illustrated in FIG. 2). Each flow balancer 255 may have the form of, for example, but not limiting of, a wire mesh screen. The flow balancers 255 may guide the flow in a uniform manner over the sampling coupons 265. The upstream flow balancer 255 may also prevent debris and other foreign objects from striking the sampling coupons 265. The downstream flow balancer 255 may prevent also debris and other foreign objects within the sampling unit 230 from exiting the sampling chamber 240 and entering the inlet system 100. The size of each flow balancer 255 may be sufficient to cover the diameter of the supply line 215 or the discharge line 225.

The sampling unit 230 may have the form of a box that encloses the aforementioned components. In an alternate embodiment of the present invention, the sampling unit 230 may have the form of a twin walled structure with insulation 260 between the twin walls. Here, a metal flange may link the twin walls and cover a portion of the insulation 260, as illustrated in FIGS. 3 and 4. The insulation 260 may ensure that the sampling chamber 240 is insulated from external heat. The insulation 260 may aide in maintaining the sampling chamber 240 at a temperature and humidity similar to the area of inlet system 100 where the airstream derived. The insulation 260 may have the form for example, but not limiting of, a rockwool type substance, or the like. In an embodiment of the present invention, the insulation 260 may have a thickness of from about 25 millimeters to about 75 millimeters.

As illustrated in FIG. 4, the sampling coupons 265 may have a rectangular shape; and are as secured to the mounting system 245. The mounting system 245 may arrange the sampling coupons 265 such that each sampling coupon 265 is electrically isolated from the other sampling coupons 265. An embodiment of the mounting system 245 may arrange the sampling coupons 265 for example, but not limiting of, in a vertical arrangement.

An embodiment of the present invention may use sampling coupons 265 made of materials, such as, but not limiting of, carbon steels, alloy steels, copper, aluminum, zinc, other alloys, or the like. An embodiment of the present invention may provide a sampling unit 230 with a mounting system 245 capable of securing approximately 50 sampling coupons 265. The sampling unit 230 of an embodiment of the present invention may include various types of sampling coupons 265 created from differing types of materials. This may allow a user to collect data on different types of corrosives present in the airstream. This may also allow a user to use a sampling coupon 265 created out of the compressor 145 component material.

In use, portions of the inlet system 100, the sampling unit 230, the supply line 215, and the discharge line 225 connect to create a closed loop flow path. The air amplifier 220 generally attempts to keep the sampling unit 230 at a pressure similar to that of the pressure within the inlet system 100. The sampling unit 230 may receive small portions of the airstream, which flows over each sampling coupon 265. Eventually the corrosives in the airstream may cause the sampling coupons 265 to fail. The flow balancers 255 prevent the failed sampling coupon(s) 265 from entering the inlet system 100. While the turbomachine operates, a user may replace the failed coupon 265 with a new coupon 265. The failed coupon 265 may be analyzed to determine, for example, but not limiting of, the type and severity of the corrosives within the airstream.

In an embodiment of the present invention, the flowrate of the airstream from range from about 100 lb/sec to about 2000 lb/sec. The pressure at a location adjacent to where the supply line 215 enters the sampling chamber 240 may range from about ambient pressure to about 0.5 inches of water column. The pressure at a location adjacent to where the discharge line 225 connects to sampling unit 230 may range from about 1.0 inches of water column to about 3.0 inches of water column. The flowrate of the airstream inside the sampling chamber 240 varies on the number of sampling coupon 265 within the box; and may range from about 10 CFM to about 100 CFM. The sampling unit 230 may be created out of any material(s) capable of withstanding the aforementioned pressures and flow rates, and the environment elements to which the sampling unit 230 may be exposed. For example, but not limiting of, an embodiment of the sampling unit 230 may be created out of a stainless steel.

Although the present invention has been shown and described in considerable detail with respect to only a few exemplary embodiments thereof, it should be understood by those skilled in the art that we do not intend to limit the invention to the embodiments since various modifications, omissions and additions may be made to the disclosed embodiments without materially departing from the novel teachings and advantages of the invention, particularly in light of the foregoing teachings. Accordingly, we intend to cover all such modifications, omission, additions and equivalents as may be included within the spirit and scope of the invention as defined by the following claims.

What is claimed is:

1. A sampling system for an inlet system, the sampling system comprising:
    at least one sampling unit for measuring corrosives within the airstream flowing within the inlet system, the at least one sampling unit comprising:
        a lid for accessing an internal portion of the at least one sampling unit;
        a sampling chamber within the internal portion, wherein the sampling chamber comprises:
            a mounting system for securing at least one sampling coupon, wherein the mounting system defines at least one position; wherein the mounting system allows for the at least one sampling coupon to be secured at the at least one position;
            a flow straightener for directing the airstream to flow over the at least one sampling coupon, wherein the flow straightener comprises an upstream portion located adjacent a supply line and a downstream portion located adjacent a discharge line; wherein the upstream and downstream portions extend approximately the width of the sampling chamber;
            a flow balancer for filtering foreign objects from the airstream, wherein the depth of the flow balancer nearly equals the depth of the sampling chamber; and wherein the flow balancer is located between the downstream portion of the flow straightener and the discharge line; and
        an air amplifier for assisting with moving the airstream through the sampling chamber;
        wherein portions of the airstream enter a supply line, flow through the sampling chamber, exit via a discharge line and reenter the inlet system.

2. The system of claim 1, further comprising insulation for reducing the effect of external weather conditions on the environment of the sampling chamber; wherein the insulation is positioned between the external perimeter of the at least one sampling unit and the boundaries of the sampling chamber.

3. The system of claim 1, wherein the lid comprises an external section and an internal section, wherein the external section encloses the sampling unit and shields the internal section.

4. The system of claim 3, wherein the internal section is comprised of a transparent material allowing for viewing the sampling chamber while the lid is closed.

5. The system of claim 3, wherein the external section is comprised of a material that protects the internal section and the internal portion of the sampling unit from environmental effects, wherein the environmental effects comprises at least one of: ultraviolent rays, radiation heating, debris, precipitation or combinations thereof.

6. The system of claim 1, wherein the sampling system is mounted outside of the inlet system.

7. The system of claim 1, wherein the sampling system is adapted to operate with a turbomachine.

8. The system of claim 1, wherein the mounting system comprises at least one shelf capable of securing a plurality of sampling coupons within the sampling chamber.

9. The system of claim 1, wherein the inlet system comprises an inlet filter house; and wherein a first sampling unit is located upstream of the inlet filter house and a second sampling unit is located downstream of the inlet filter house.

10. The system of claim 1, wherein each sampling coupon measures corrosion from of at least one of: chloride, sulfide, stress, or combinations thereof.

11. The system of claim 1, wherein the sampling coupon is created from at least one of the followings materials: carbon steel, copper, aluminum, zinc, alloy steel, or combinations thereof.

12. The system of claim 1, wherein the pressure of the airstream comprises a range of from about 0.5 inches of water column to about negative 5.0 inches of water column.

13. The system of claim 8, wherein the mounting system electrically isolates each sampling coupon from other sampling coupons.

14. The system of claim 1, further comprising a second flow balancer located between the upstream portion of the flow straightener and the supply line.

15. The system of claim 1, further comprising a weather hood for shielding the sampling unit from precipitation and other weather conditions, and wherein the weather hood comprises a series of ventilation holes allowing for increased air circulation through the weather hood.

16. The system of claim 8, wherein the plurality of sampling coupons are arranged to allow for a nearly uniform flow of the airstream across each of the plurality of sampling coupons.

17. The system of claim 9, wherein each sampling unit allows for the sampling chamber to be accessed while the sampling unit operates.

18. The system of claim 17, wherein each sampling unit allows for a single sampling coupon to be removed while the sampling unit operates.

19. A system recording corrosives within an airstream entering a turbomachine, the system comprising:
    an inlet system for receiving and directing air into a compressor of the turbomachine, wherein the inlet system comprises at least one of the following:
        an inlet filter house for screening the airstream entering the inlet system;
        a cooling module for conditioning the airstream within the inlet system;
        a silencer section for reducing the noise within the inlet system: and
        an inlet bleed heat system for conditioning the airstream:
    a sampling system mounted outside of an inlet system, the sampling system comprising:
        at least one sampling unit for recording the level of corrosives in the airstream, the at least one sampling unit comprising:
            a lid for covering internal components of the at least one sampling unit; wherein the lid is created from a material that allows for viewing the internal components after the lid is closed;
a sampling chamber within the sampling unit, wherein the sampling chamber comprises:
a shelf for supporting sampling coupons within the sampling chamber, wherein the shelf includes individual positions and allows for each sampling coupon to be secured at an individual position;
a flow straightener for directing the airstream to flow in a nearly uniform manner over each sampling coupon, wherein the flow straightener comprises an upstream portion located positioned adjacent a supply line and a downstream portion positioned located adjacent a discharge line; wherein the upstream and downstream portions are in parallel position and extended approximately the width of the sampling chamber;
a flow balancer for preventing the chance of a foreign objects from entering the inlet system, wherein the depth of the flow balancer nearly extends to the depth of the sampling chamber; and wherein the flow balancer is located between the downstream portion of the flow straightener and the discharge line; and
an air amplifier for moving the airstream throughout the sampling chamber and for returning the airstream back into inlet system;
wherein portions of the airstream enter a supply line, flow through the sampling chamber, exit via a discharge line and reenter the inlet system.

20. The system of claim 19, further comprises a second flow balancer for reducing the amount of a foreign objects entering the inlet system, wherein the depth of the flow balancer nearly extends to the depth of the sampling chamber; and wherein the flow balancer is located between the upstream portion of the flow straightener and the supply line.

21. The system of claim 19, further comprising a weather hood for shielding the sampling unit from precipitation and other weather conditions, wherein the weather hood comprises a series of ventilation holes allowing for increased air circulation through the weather hood.

22. The system of claim 19, wherein the sampling coupons are arranged to allow for a nearly uniform flow across each coupon.

23. The system of claim 19, wherein the sampling unit allows for the internal components of the sampling unit to be accessed while the sampling unit is in operation.

24. The system of claim 23, wherein each sampling unit allows for each sampling coupon to be removed while the sampling unit operates.

25. The system of claim 19, further comprising insulation for reducing the effect of external weather conditions on the environment of the sampling chamber; wherein the insulation is positioned between the external perimeter of the at least one sampling unit and the boundaries of the sampling chamber.

26. The system of claim 19, wherein the lid comprises an external section and an internal section, wherein the external section encloses the sampling unit and shields the internal section.

27. The system of claim 26, wherein the internal section is comprised of a transparent material allowing for viewing the sampling chamber while the lid is closed.

28. The system of claim 26, wherein the external section is comprised of a material that protects the internal section and the internal portion of the sampling unit from environmental effects, wherein the environmental effects comprises at least one of: ultraviolent rays, radiation heating, debris, precipitation or combinations thereof.

* * * * *